United States Patent [19]

Peden et al.

[11] Patent Number: 4,582,225
[45] Date of Patent: Apr. 15, 1986

[54] LAZY SUSAN PORCELAIN POWDER DISPENSER

[76] Inventors: Craig A. Peden; Kim A. Peden, both of P.O. Box 781, Collegedale, Tenn. 37315

[21] Appl. No.: 625,798

[22] Filed: Jun. 28, 1984

[51] Int. Cl.$^4$ .............................................. B67D 5/52
[52] U.S. Cl. ................... 222/135; 222/144; 222/361; 312/252; 211/163
[58] Field of Search ................. 22/135, 144, 339, 511, 22/361; 221/132, 119; 312/252, 97.1, 125; 211/163, 194, 205

[56] References Cited

U.S. PATENT DOCUMENTS

| | | | |
|---|---|---|---|
| 258,467 | 5/1882 | Palmer | 222/144 |
| 277,384 | 5/1883 | Turner | 222/511 |
| 280,979 | 7/1883 | Westphal | 222/144 |
| 411,123 | 9/1889 | Harigel | 222/144 |
| 888,464 | 5/1908 | Burri et al. | 222/144 |
| 1,038,198 | 9/1912 | Randall et al. | 211/205 |
| 1,183,111 | 5/1916 | Pettermann et al. | 222/368 |
| 1,426,844 | 8/1922 | Wood | 312/97.1 |
| 3,682,356 | 8/1972 | Kaxle | 222/144 |

FOREIGN PATENT DOCUMENTS

WO80/00523  4/1980  PCT Int'l Appl. ............... 211/163

*Primary Examiner*—H. Grant Skaggs
*Attorney, Agent, or Firm*—Harvey B. Jacobson

[57] ABSTRACT

Base structure is provided from which an upstanding post is supported and separate top and bottom horizontal support plates are mounted on the post in vertically spaced relation and for rotation relative thereto. Sleeve structure is also rotatable on the post and disposed between and keys the plates against rotation relative to each other. A plurality of upright tubular fluent material reservoirs are supported from and extend between corresponding peripheral portions of the plates spaced about and outward from the post and the upper and lower ends of the reservoirs open upwardly and downwardly through the upper and lower plates, respectively. Manually actuatable dispensing structure is carried by the lower end of each reservoir and a horizontal closure plate is mounted on the post above the upper plate for rotation relative to and about the post. The closure plate includes outer peripheral portions overlying the upper ends of the reservoirs and one of the outer peripheral portions includes a vertical opening formed therethrough selectively registrable with the upper ends of the reservoirs upon angular displacement of the closure plate relative to the top plate. The closure plate is mounted on the post in friction connection with the top plate, whereby the cover plate will rotate with the top and bottom plates and yet may be rotated relative to the post independent of rotation of the top and bottom plates.

7 Claims, 7 Drawing Figures

LAZY SUSAN PORCELAIN POWDER DISPENSER

BACKGROUND OF THE INVENTION

Dental laboratories may stock and use literally hundreds of different shades of porcelain powder and the porcelain powder usually is contained within small one ounce bottles. If a particular shade of porcelain powder is needed, the cap upon the bottle must be removed, the desired quantity of porcelain powder is removed and the cap of the bottle must then be replaced before the bottle may be returned to its proper place. Handling of a small bottle of this type can often result in spillage of some of the porcelain powder therefrom and the return of spilled porcelain powder to the bottle can cause the powder to become contaminated.

Accordingly, a need exists for a porcelain powder dispenser which may house numerous different shades of porcelain powder and from which a quantity of the desired shade of porcelain powder may be readily and quickly dispensed. Previously known dispensers including some of the general structural and operational features of the instant invention are disclosed in U.S. Pat. Nos. 277,384, 398,383, 411,123, 888,464, 1,183,111 and 3,682,356. However, these previously known forms of dispensers have not been specifically designed for use in conjunction with fluent powder materials which must be maintained free of contamination and which are to be selectively dispensed in small quantities.

BRIEF DESCRIPTION OF THE INVENTION

The dispenser of the instant invention includes a plurality of upstanding tubular reservoirs arranged in a circle pattern about and supported from a support post for simultaneous angular displacement about the post. Each of the reservoirs may be constructed of a transparent material, thereby enabling the color shade of the material within each reservoir to be readily ascertained. Each reservoir includes a push-button actuated dispensing mechanism at the lower end thereof by which a predetermined measured quantity of fluent granular material may be dispensed from the lower end of each reservoir. The upper and lower ends of the reservoirs are supported from and extend through corresponding peripheral portions of upper and lower circular plates mounted from the post in vertically spaced relation and for rotation relative thereto. A sleeve is journaled on the post between the upper and lower plates and keys the latter together against rotation relative to each other and a closure plate is rotatably mounted from the upper end of the post closely above the upper ends of the reservoirs. The closure plate outer peripheral portions overlie the upper ends of the reservoirs and one of the outer peripheral portions of the closure plate includes an opening formed therethrough selectively registrable with each reservoir open upper end. The closure plate is mounted on the post for rotation relative to the upper and lower plates, but is frictionally connected with the upper plate whereby the closure plate will rotate with the upper and lower plates relative to the post until such time as sufficient forces are applied to the upper and closure plates in order to effect relative angular displacement thereof.

The main object of this invention is to provide a dispenser which may be utilized to contain and dispense individual color shades of porcelain powder.

Another object of this invention is to provide a dispenser constructed in a manner whereby the color shades of porcelain powders supported therefrom may be readily ascertained and the dispenser may be quickly utilized to dispense a measured quantity of a selected color of porcelain powder.

Still another important object of this invention is to provide a dispenser constructed in a manner whereby the powder stored thereby and to be dispensed therefrom may be maintained in a non-contaminated condition and further constructed in a manner such that the desired quantity of a selected shade of porcelain powder may be dispensed therefrom without spillage of any of the porcelain powder.

Another important object of this invention is to provide a powder dispenser in accordance with the preceding objects and constructed in a manner whereby the plurality of powder reservoirs thereof may have the supply of powders disposed therein readily replenished.

Another object of this invention is to provide a dispenser for porcelain powders and which may be utilized to support and dispense a plurality of different powders and with the dispenser occupying a relatively small plan area of a suitable support surface such as a workbench.

A final object of this invention to be specifically enumerated herein is to provide a dispenser in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 3 is a fragmentary horizontal sectional view taken substantially upon the plane indicated by the section line 3—3 of FIG. 2;

FIG. 6 is a fragmentary perspective view illustrating the structure by which a center sleeve portion is utilized to key a pair of upper and lower plates rotatably mounted on a support post against relative angular displacement; and FIG. 7 is a fragmentary vertical sectional view illustrating the manner in which a funnel may be used to replenish the supply of fluent granular material in one of the tubular reservoirs through an access opening registered therewith and formed in a closure plate overlying the upper ends of the reservoirs.

DETAILED DESCRIPTION OF THE INVENTION

Figure 1:
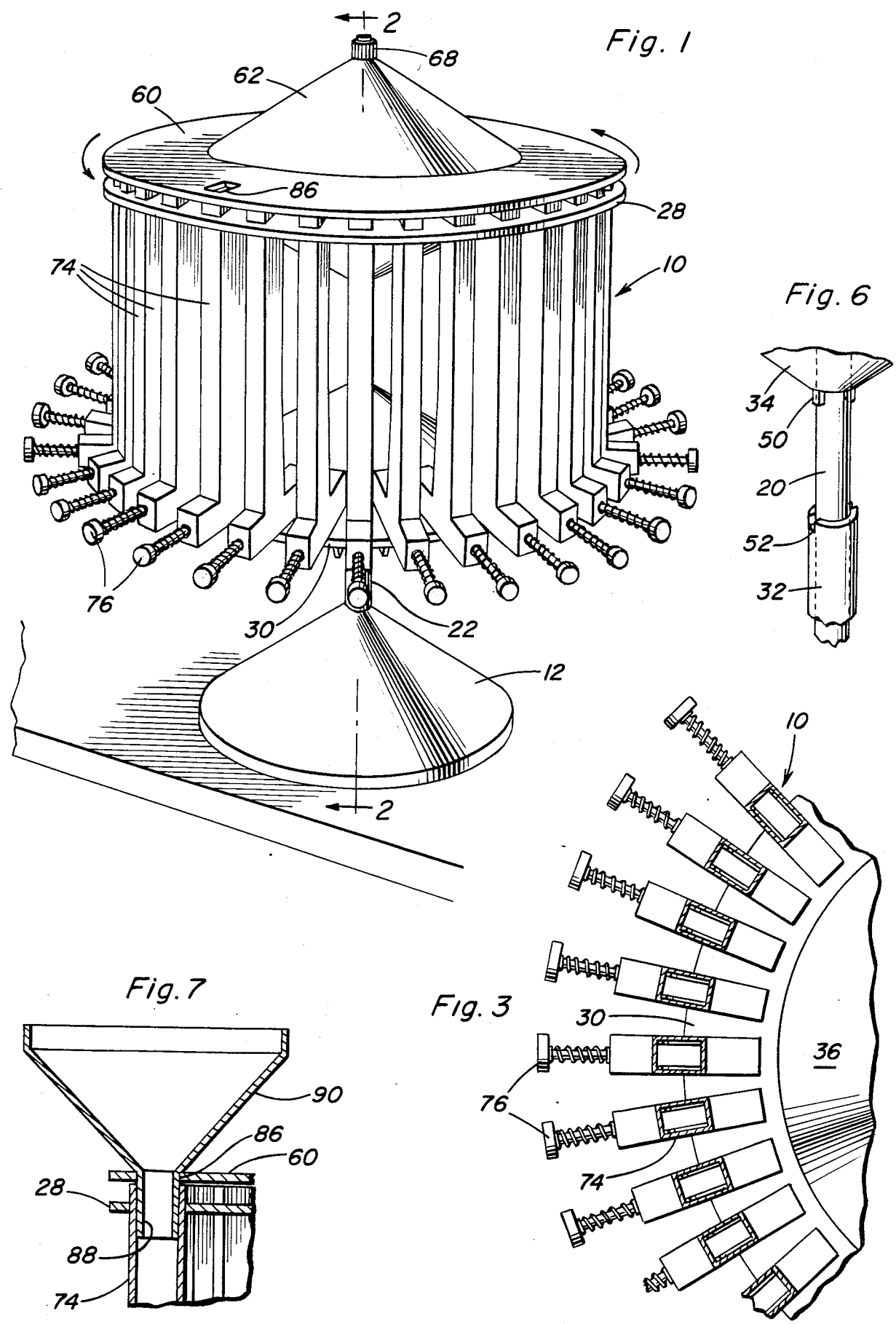
FIG. 1 is a perspective view of a dispenser constructed in accordance with the present invention.

Referring now more specifically to the drawings the numeral 10 generally designates the dispenser of the instant invention. The dispenser 10 includes a hollow weighted base of substantial but limited horizontal plan area defining a centrally disposed upwardly opening recess 14 closed at its lower end by a centrally apertured end wall 16 defining the upper extremity of a central downwardly opening recess 18. The lower end of a cylindrical post 20 is seated within the recess 14 and includes a diametrically reduced threaded shank 22 which projects and is removably secured through the apertured end wall 16 by a threaded nut 24 within the recess 18.

A first spacing sleeve 26 is rotatably mounted on the post 20 immediately above the base 12 and is downwardly abutted against and thus frictionally engages the upper portion of the base 12 disposed immediately about the post 20. A pair of relatively inverted and large and small diameter top and bottom plates 28 and 30 are rotatably mounted on the post 20 above the spacing sleeve 26 and have a second spacing sleeve 32 also rotatably mounted on the post 20 interposed therebetween. The plates 28 and 30 include inverted and upright central conical portions 34 and 36, respectively, and the central portions 34 and 36 include coaxial sleeve portions 38 and 40. The sleeve portion 30 downwardly abuts the upper end of the spacing sleeve 26, the spacing sleeve 32 downwardly abuts the upper end of the sleeve portion 40 and the sleeve portion 38 downwardly abuts the upper end of the second spacing sleeve 32.

The upper end of the sleeve 26 includes diametrically opposite upwardly projecting tongues 42 receivable in downwardly opening diametrically opposite recesses 44 formed in the lower end of the sleeve portion 40, the upper end of the sleeve portion 40 includes diametrically opposite tongues 46 receivable in diametrically opposite downwardly opening recesses 48 formed in the lower end of the spacing sleeve 32, the lower end of the sleeve portion 38 includes diametrically opposite tongues 50 received in diametrically opposite recesses 52 formed in the upper end of the spacing sleeve 32 and an axially short spacing sleeve 54 rotatable on the post 20 includes diametrically opposite tongues 56 downwardly receivable in upwardly opening diametrically opposite recesses 58 formed in the upper end of the sleeve portion 38. Accordingly, the sleeves 26, 32 and 54 as well as the sleeve portions 38 and 40 are keyed together for simultaneous rotation relative to the post 20.

A closure plate 60 is provided and includes an upright conical central portion 62 as well as a central sleeve portion 64 and the sleeve portion 64 is rotatably received on the post 20 above the spacing sleeve 54 and downwardly abuts the latter. The upper end of the post 20 includes a threaded terminal end 66 with which a nut 68 is threadingly engaged, but the nut 68 does not tightly engage the upper end of the sleeve portion 64.

Figure 2:
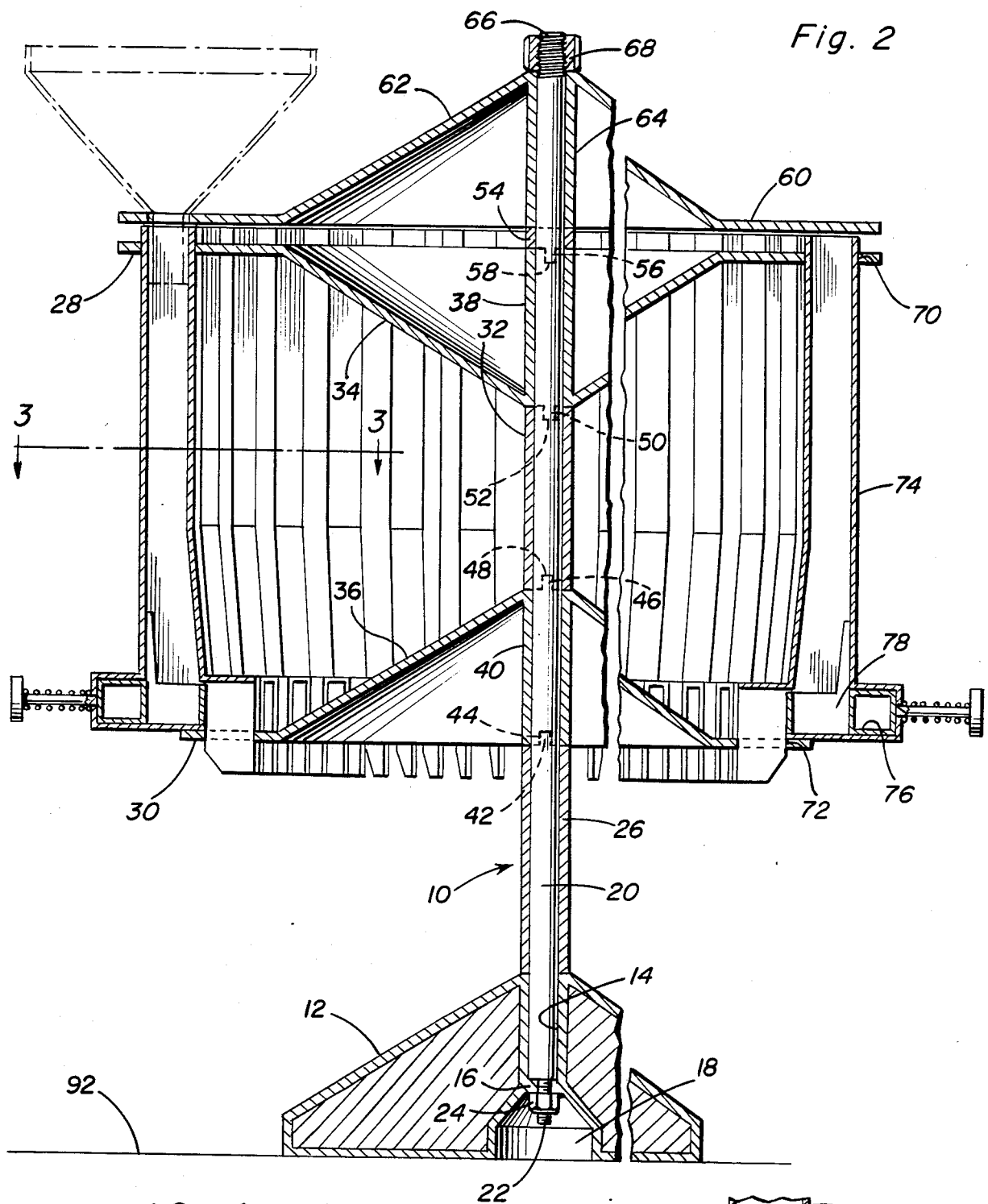
FIG. 2 is an enlarged fragmentary vertical sectional view taken substantially upon the plane indicated by the section line 2—2 of FIG. 1.
Figure 4:
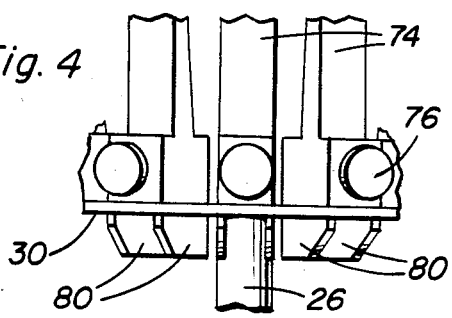
FIG. 4 is a fragmentary elevational view of one lower peripheral portion of the rotatable reservoir portion of the dispenser.
Figure 5:
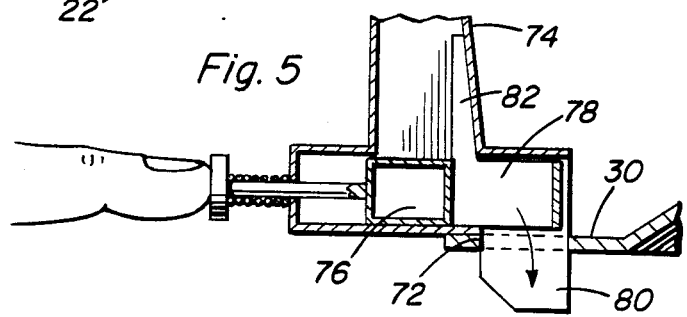
FIG. 5 is a fragmentary vertical sectional view taken substantially upon a plane passing through the center of the assemblage illustrated in FIG. 4.

The outer peripheral portions of the closure plate 60 are spaced slightly above corresponding outer peripheral portions of the top plate 28. Corresponding outer peripheral portions of the top and bottom plates 28 and 30 include vertical openings 70 and 72 formed therethrough and the upper and lower ends of a plurality of upstanding tubular powder reservoirs 74 are snugly received through the openings 70 and 72. In addition, the lower end of each reservoir 74 includes a spring-biased plunger-type dispenser 76 defining an upwardly and downwardly opening material receiving pocket 78 which opens upwardly into the lower end of the associated reservoir 74 when the dispenser 76 is at its outermost limit position and opens downwardly through the lower end of the reservoir and the opening 72 when the dispenser 76 is displaced generally radially inwardly toward the post 20 to its innermost limit position. Of course, the dispenser 76 may thus be utilized to selectively dispense predetermined measured quantities of powder from the corresponding reservoir each time the dispenser 76 is displaced inwardly from its outermost position thereof illustrated in FIG. 2 toward its innermost limit position illustrated in FIG. 5. Opposite side portions of the lower end of each reservoir 74 include opposite side flanges 80 which are downwardly received through the corresponding opening 72 and each dispenser 76 includes a pair of upwardly projecting opposite side fingers 82 which transverse the lower end of the corresponding reservoir 74 during actuation of the dispenser 76 in order to prevent caking of the powder material within the lower end of the reservoir 74.

It will be noted that the lower end of each reservoir 74 downwardly abuts and is therefore supported by a corresponding outer peripheral portion of the bottom plate 30 and that the open upper ends of the reservoirs 74 are closely closed by the closure plate 60. However, one peripheral portion of the closure plate 60 includes an opening 86 formed therethrough selectively registrable with each reservoir upper open end and in which the diametrically reduced outlet end 88 of an upwardly opening funnel 90 may be engaged for telescopic engagement of the funnel outlet end 88 in the upper end of the reservoir 74 with which the opening 86 is registered.

Inasmuch as the various previously mentioned components which are keyed together and rotatably supported from the post 20 cannot be rotated independent of each other, the rotary portion of the dispenser 10 may be rotated either by turning the spacing sleeve 26, the top and bottom plates 28 and 30 or engaging and angularly displacing one or more of the reservoirs 74 about the support post 26.

Inasmuch as the cover plate sleeve portion 64 is downwardly abutted against the sleeve 54 and the latter is keyed to the plates 28 and 30 for rotation therewith, frictional engagement between the sleeve portion 64 and the sleeve 54 causes the cover plate 60 to rotate with the reservoirs 74. Further, the peripheral spacing between adjacent reservoirs 74 is greater than the width of the reservoirs 74 and the width of the opening 86. Thus, the cover plate 60 may be turned to a position with the opening 86 out of registry with any of the reservoirs 74 and subsequent angular displacement of the reservoirs 74 about the post 20 will not cause angular displacement of the reservoirs 74 relative to the cover plate 60. However, when it is desired to replenish the supply of powder within one of the reservoirs 74, the reservoir 74 may be held against rotation about the post 20 and the cover plate 60 may be angularly displaced to a position with the opening 86 registered with the reservoir 74 in which the supply of powder is to be replenished. Then, the supply of powder within that reservoir may be replenished by using the funnel 90 in the manner illustrated in FIG. 7 of the drawings. After the supply of powder within a reservoir 74 has been replenished, the funnel 90 may be removed and the closure plate 60 may again be rotated to a position with the opening 86 out of registry with any of the reservoirs 74.

It is believed apparent that since the dispenser 10 is to be used in conjunction with porcelain powders of different shades of color, the reservoirs 74 may be constructed of transparent material. Further, when the dispenser 10 is disposed on a suitable support surface such as the support surface 92 illustrated in FIG. 2, the lower ends of the reservoirs 74 are spaced appreciably above the surface 92, thus enabling the space disposed closely about the base 12 on the surface 92 to be used for supporting low height attendant equipment.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A fluent material dispenser including base means, an upright post, the lower end of said post being stationarily mounted from said base means for support of said post in an upright position from a support surface upon which said base means rests, separate top and bottom horizontal support plates mounted on said post in vertically spaced relation and for rotation relative to and about said post, sleeve means rotatable on said post and keyed to each plate and thereby interconnecting said plates against rotation relative to each other, a plurality of upright tubular fluent material reservoirs supported from and extending between corresponding peripheral portions of said plates spaced about and outward from said post, the upper and lower ends of said reservoirs opening upwardly and downwardly through said top and bottom plates, respectively, manually actuatable dispensing means carried by the lower end of each reservoir and operable to dispense a predetermined quantity of fluent material from the corresponding reservoir, a horizontal closure plate mounted on said post above said top plate and for rotation relative to and about said post, said closure plate includng outer peripheral portions closely overlying the upper ends of said reservoirs, one of said outer peripheral portions including a single vertical opening formed therethrough selectively registrable with the upper ends of said reservoirs upon angular displacement of said closure plate about said post relative to said top plate, said sleeve means including a first lower sleeve rotatably mounted on said post above and downwardly frictionally abutted against opposing upper surface portions of said base disposed about said post, said bottom plate including a central supportive sleeve portion rotatably mounted on said post and downwardly abutted against the upper end of said first sleeve and keyed thereto for rotation therewith, said sleeve means further including a second sleeve rotatably mounted on said post and downwardly abutted against the upper end of said sleeve portion and keyed thereto for rotation therewith, said top plate including a central supportive sleeve portion rotatably mounted on said post and downwardly abutted against and keyed to the upper end of said second sleeve portion for rotation therewith, said closure plate including a central supportive sleeve portion rotatably mounted on said post above said top plate sleeve portion and downwardly fricitonally abutted thereagainst for rotation therewith, whereby said closure plate will rotate with said top plate when said top and the bottom plates are rotated relative to said post, and yet said closure plate may be rotated relative to said post independent of rotation of said top and bottom plates relative to said post.

2. The dispenser of claim 1 wherein said base means is weighted and includes downwardly facing lower surface means for support from a horizontal surface.

3. The dispenser of claim 1 wherein said top and bottom plates include inverted and upright conical central portions, respectively.

4. The dispenser of claim 1 wherein said dispensing means each includes an actuator therefor shiftable generally radially of said post and spring-biased toward a radial outermost position.

5. The dispenser of claim 4 wherein said dispensing means each includes means operable to prevent gravity flow of fluent material from the lower end of the corresponding reservoir when the actuator is in the outermost position and to dispense said predetermined quantity of fluent material from the lower end of the corresponding reservoir responsive to shifting of the actuator toward a radial innermost position thereof.

6. The dispenser of claim 5 wherein said base means is weighted and include downwardly facing lower surface means for support from a horizontal surface.

7. The dispenser of claim 6 wherein said top and bottom plates include inverted and upright conical central portions, respectively.

* * * * *